US00PP23826P2

(12) United States Plant Patent
Valin

(10) Patent No.: US PP23,826 P2
(45) Date of Patent: Aug. 13, 2013

(54) ***BEGONIA* PLANT NAMED 'TMBEG096'**

(50) Latin Name: *Begonia×tuberhybrida*
Varietal Denomination: TMBEG096

(75) Inventor: Charles Valin, Ipswich (GB)

(73) Assignee: Thompson + Morgan (UK) Ltd., Ipswich, Suffolk (GB)

( * ) Notice: Subject to any disclaimer, the term of this patent is extended or adjusted under 35 U.S.C. 154(b) by 74 days.

(21) Appl. No.: 13/317,161

(22) Filed: Oct. 11, 2011

(51) Int. Cl.
*A01H 5/00* (2006.01)

(52) U.S. Cl.
USPC ..... Plt./347; Plt./343; Plt./344

(58) Field of Classification Search
USPC ..... Plt./343, 344, 347
See application file for complete search history.

*Primary Examiner* — Susan McCormick Ewoldt
(74) *Attorney, Agent, or Firm* — C. A. Whealy

(57) ABSTRACT

A new and distinct cultivar of *Begonia* plant named 'TMBEG096', characterized by its upright to spreading and mounded plant habit; moderately freely basal branching habit; freely and continuously flowering habit; fragrant flowers; single and double flowers that are orange, orange red and yellow in color.

2 Drawing Sheets

Botanical designation: *Begonia×tuberhybrida*.
Cultivar denomination: 'TMBEG096'.

BACKGROUND OF THE INVENTION

The present invention relates to a new and distinct cultivar of *Begonia* plant, botanically known as *Begonia×tuberhybrida*, and hereinafter referred to by the name 'TMBEG096'.

The new *Begonia* plant is a product of a planned breeding program conducted by the Inventor in Harkstead, Ipswich, United Kingdom. The objective of the breeding program was to develop new trailing *Begonia* plants with fragrant flowers.

The new *Begonia* plant originated from a cross-pollination made by the Inventor in August, 2008 of a proprietary selection of *Begonia×tuberhybrida* identified as code number BG07074A, not patented, as the female, or seed, parent with a proprietary selection of *Begonia×tuberhybrida* identified as code number BG07074B, not patented, as the male, or pollen, parent. The new *Begonia* plant was discovered and selected by the Inventor as a single flowering plant from within the progeny of the stated cross-pollination in a controlled greenhouse environment in Harkstead, Ipswich, United Kingdom in July, 2009.

Asexual reproduction of the new *Begonia* plant by shoot tip cuttings in a controlled greenhouse environment in Harkstead, Ipswich, United Kingdom since August, 2009 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'TMBEG096'. These characteristics in combination distinguish 'TMBEG096' as a new and distinct *Begonia* plant:

1. Upright to spreading and mounded plant habit.
2. Moderately freely basal branching habit.
3. Freely and continuously flowering habit.
4. Fragrant flowers.
5. Single and double flowers that are orange, orange red and yellow in color.

Plants of the new *Begonia* can be compared to plants of the female parent selection. Plants of the new *Begonia* differ from plants of the female parent selection in the following characteristics:

1. Plants of the new *Begonia* have darker green-colored leaves than plants of the female parent selection.
2. Plants of the new *Begonia* and the female parent selection differ in flower color as plants of the female parent selection have light yellow and orange-colored flowers.
3. Flowers of plants of the new *Begonia* are more fragrant than flowers of plants of the female parent selection.

Plants of the new *Begonia* can be compared to plants of the male parent selection. Plants of the new *Begonia* differ from plants of the male parent selection in the following characteristics:

1. Plants of the new *Begonia* are more freely flowering than plants of the male parent selection.
2. Plants of the new *Begonia* have double and single flowers whereas plants of the male parent selection have semi-double flowers.
3. Plants of the new *Begonia* and the male parent selection differ slightly in flower color.
4. Flowers of plants of the new *Begonia* are more fragrant than flowers of plants of the male parent selection.

Plants of the new *Begonia* can be compared to plants of the *Begonia* 'Encanto Orange', disclosed in U.S. Plant Pat. No. 20,898. In side-by-side comparisons conducted in Harkstead, Ipswich, United Kingdom, plants of the new *Begonia* differed from plants of 'Encanto Orange' in the following characteristics:

1. Plants of the new *Begonia* had larger and darker green-colored leaves than plants of 'Encanto Orange'.
2. Plants of the new *Begonia* had larger flowers than plants of 'Encanto Orange'.

3. Plants of the new *Begonia* had larger flowers than plants of 'Encanto Orange'.
4. Plants of the new *Begonia* had double and single flowers whereas plants of 'Encanto Orange' only had single flowers.
5. Plants of the new *Begonia* and 'Encanto Orange' differed in flower color as plants of 'Encanto Orange' had bright orange-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'TMBEG096' grown in a container.

The photograph on the second sheet are close up views of upper and lower surfaces of typical double and single flowers and upper and lower surfaces of typical leaves of 'TMBEG096'.

DETAILED BOTANICAL DESCRIPTIONS

Plants used for the aforementioned photographs and following observations and measurements were grown in 12-cm containers during the summer in a glass-covered greenhouse in Maasdijk, The Netherlands. During the production of the plants, day temperatures ranged from 18° C. to 19° C. and night temperatures averaged 17° C. Plants were 14 weeks old when the photographs and the description were taken. In the following description, color references are made to The Royal Horticultural Society Colour Chart, 2007 Edition, except where general terms of ordinary dictionary significance are used.

Botanical classification: *Begonia×tuberhybrida* 'TMBEG096'.

Parentage:

*Female, or seed, parent*.—Proprietary selection of *Begonia×tuberhybrida* identified as code number BG07074A, not patented.

*Male, or pollen, parent*.—Proprietary selection of *Begonia×tuberhybrida* identified as code number BG07074B, not patented.

PROPAGATION:

*Type*.—By tip cuttings.

*Time to initiate roots*.—About 20 days at temperatures of about 25° C.

*Time to produce a rooted young plant*.—About 40 to 42 days at temperatures of about 21° C. to 23° C.

*Root description*.—Medium in thickness, fibrous; white in color; plants of the new *Begonia* have not been observed to form tubers.

*Rooting habit*.—Moderately freely branching; medium density.

Plant description:

*Plant form and growth habit*.—Upright to spreading and mounded plant habit; flattened globular in shape; moderately freely basal branching with about four primary branches per plant; primary branches with secondary branches at potentially every node; moderately vigorous growth habit.

*Plant height*.—About 17 cm.

*Plant width*.—About 34.2 cm.

*Lateral branch description*.—Length: About 7.5 cm. Diameter: About 8 mm. Internode length: About 2 cm. Texture: Sparsely pubescent. Color: Close to 148B heavily tinged with close to 176B.

*Leaf description*.—Arrangement: Alternate, simple. Length: About 15 cm. Width: About 9.3 cm. Shape: Ovate to deltoid. Apex: Acute. Base: Oblique, unequal cordate. Margin: Bi-serrate. Texture, upper and lower surfaces: Sparsely pubescent; velvety. Venation pattern: Palmate; reticulate. Color: Developing leaves, upper surface: Close to 137B. Developing leaves, lower surface: Close to 146C to 146D slightly tinged with close to 172B. Fully expanded leaves, upper surface: Darker than 147A; venation, close to 146C. Fully expanded leaves, lower surface: Close to 148C to 148D strongly tinged with close to 184B; venation, between 152A and 197A. Petioles: Length: About 5.9 cm. Diameter: About 5 mm. Texture, upper and lower surfaces: Moderately pubescent. Color, upper and lower surfaces: Close to 174B; base, tinged with close to 152B to 152C; apex, close to 185A.

Flower description:

*Flowering habit*.—Double (male) and single (female) rotate flowers arranged in axillary cymes; freely flowering habit with about three flowers per cyme and about 36 flowers developing per plant; flowers and face mostly outwardly to nodding.

*Fragrance*.—Moderately fragrant; fragrance pleasant, sweet-acidic.

*Natural flowering season*.—Plants begin flowering about seven weeks after planting; long flowering period, plants flower freely and continuously from spring until autumn in The Netherlands.

*Flower longevity*.—Individual flowers last about ten days on the plant; flowers not persistent.

*Inflorescence height* (*including peduncle*).—About 16.8 cm.

*Inflorescence diameter*.—About 12.5 cm.

*Flowers*.—Female flowers, diameter: About 8.2 cm. Female flowers, depth (height): About 3.8 cm. Male flowers, diameter: About 9.5 cm. Male flowers, depth (height): About 4.8 cm.

*Flower buds*.—Length, female flowers: About 2.1 cm. Diameter, female flowers: About 8 mm to 18 mm. Length, male flowers: About 3 cm. Diameter, male flowers: About 1.3 cm to 3.5 cm. Shape, female and male flowers: Broadly ovate to nearly circular, flattened. Color, female and male flowers: Close to 34B to 34C; towards the base, close to 145C to 145D.

*Tepals*.—Quantity per flower: Female flowers, usually about four per flower; male flowers, usually about two per flower. Length, female flowers: About 4.9 cm. Width, female flowers: About 2.9 cm to 4.3 cm. Length, male flowers: About 6 cm. Width, male flowers: About 6.9 cm. Shape, female flowers: Broadly obcordate to obovate. Shape, male flowers: Broadly ovate to nearly circular. Apex, female and male flowers: Obtuse. Margin, female and male flowers: Entire. Texture, female and male flowers, upper and lower surfaces: Smooth, glabrous; velvety. Color, female and male flowers: When opening, upper surface: Close to 30C; towards the margins, close to N30B;

toward the base, close to 14B. When opening, lower surface: Close to N30A. Fully opened, upper surface: Close to 13A to 13B; towards the margins, close to between 28A and 30B; color does not fade with development. Fully opened, lower surface: Close to between 30A and N30B; color does not fade with development.

*Tepaloids*.—Quantity per flower: Present only on male flowers, usually about 65 per flower. Length: About 2.4 cm to 4.2 cm. Width: About 1.3 cm to 4 cm. Shape: Broadly obcordate to obcordate. Apex: Obtuse. Margin: Entire. Texture, upper and lower surfaces: Smooth, glabrous; velvety. Color: When opening, upper surface: Close to 8A; towards the margins, close to 24C to 24D. When opening, lower surface: Close to 10B; towards the margins, close to 29A. Fully opened, upper surface: Close to 13A to 13B; margins, close to between 28A and 30B; color does not fade with development. Fully opened, lower surface: Close to between 30A and N20B; color does not fade with development.

*Peduncles*.—Length: About 10.4 cm. Diameter: About 5 mm. Angle: About 40° from vertical. Strength: Moderately strong. Texture: Sparsely pubescent. Color: Close to 199B; distally, close to 185A.

*Pedicels*.—Length, female flowers: About 3.9 cm. Diameter, female flowers: About 2 mm. Length, male flowers: About 1.4 cm. Diameter, male flowers: About 3 mm. Angle, female flowers: About 40° from vertical. Angle, male flowers: Mostly erect. Strength, female and male flowers: Moderately strong. Texture, female and male flowers: Smooth, glabrous. Color, female and male flowers: Upper surface: Close to 146D strongly tinged with close to between 46A and 185A. Lower surface: Close to 146D.

*Reproductive organs*.—Female flowers: Number of pistils: About three per flower. Pistil length: About 7 mm. Style length: About 4 mm. Style color: Close to 14A. Stigma color: Close to 14A. Ovary color: Close to 146D; upper surface and apex strongly tinged with close to 173A. Male flowers: All stamens on male flowers transformed into tepaloids.

*Seeds and fruits*.—Seed and fruit production has not been observed on plants of the new *Begonia*.

Disease/pest resistance: Resistance to pathogens and pests common to *Begonia* has not been observed on plants of the new *Begonia*.

Temperature tolerance: Plants of the new *Begonia* have been observed to tolerate temperatures from about 12° C. to about 35° C.

It is claimed:

1. A new and distinct *Begonia* plant named 'TMBEG096' as illustrated and described.

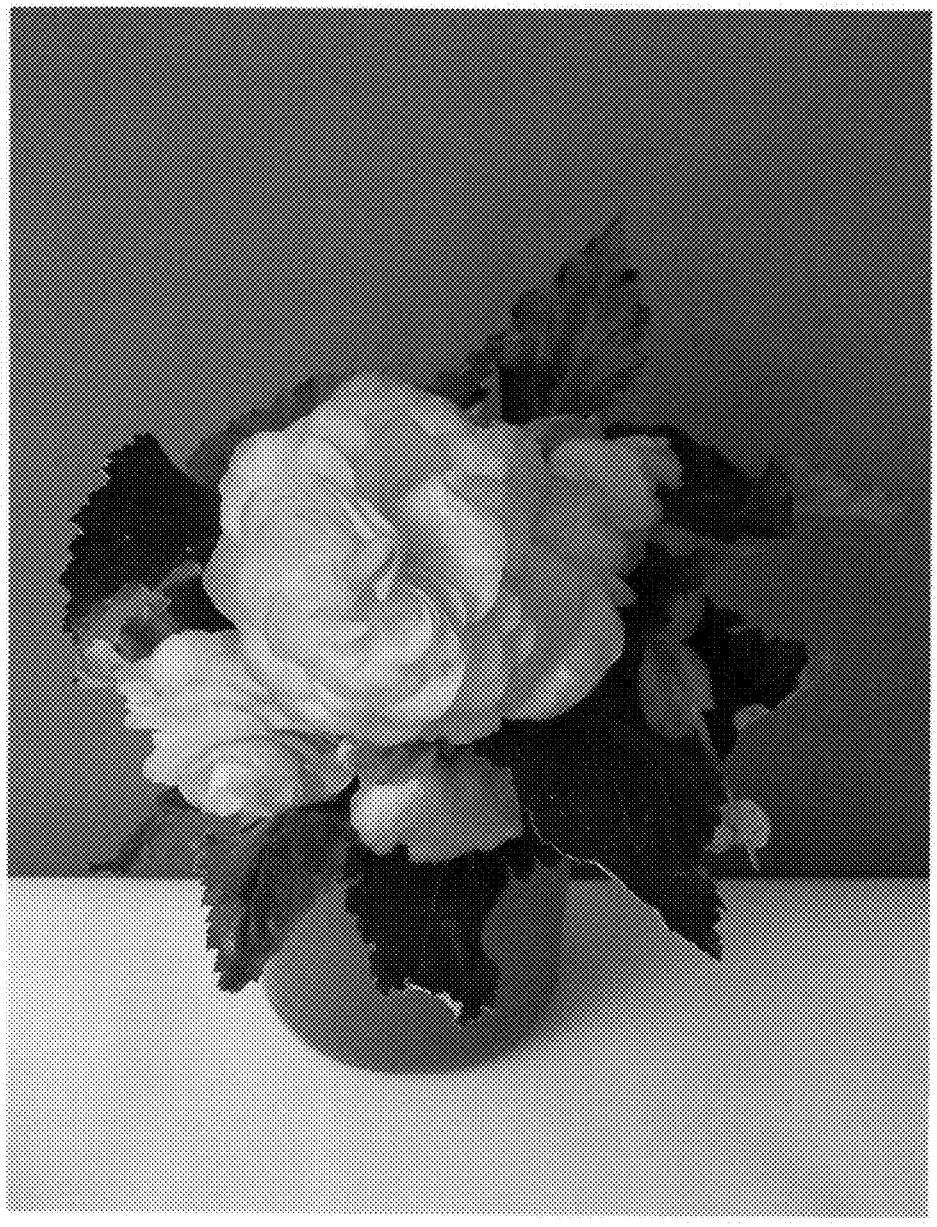

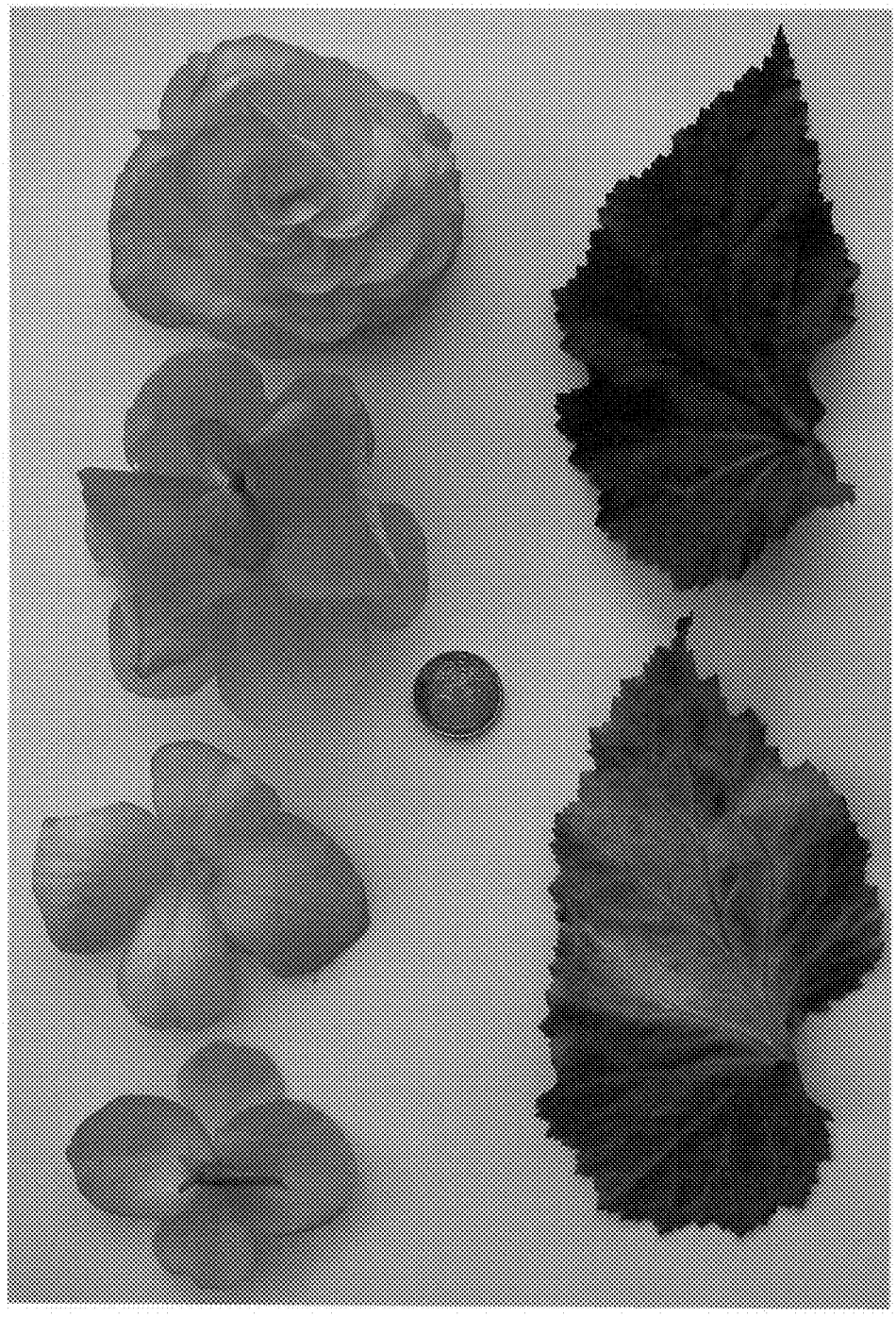

* * * * *